(12) United States Patent
Bernard et al.

(10) Patent No.: US 6,375,725 B1
(45) Date of Patent: Apr. 23, 2002

(54) END-OF-SERVICE INDICATOR INCLUDING POROUS WAVEGUIDE FOR RESPIRATOR CARTRIDGE

(75) Inventors: Pierre Bernard, St-Augustin-de-Desmaures; Serge Caron, Quebec; Marco St-Pierre, Val-Bélair; Jaime Lara, Montreal, all of (CA)

(73) Assignees: Institut National D'Optique, Saint-Foy; Institut de Recherche en Santa et Securite du Travail du Quebec, Montreal, both of (CA)

( * ) Notice: Subject to any disclaimer, the term of this patent is extended or adjusted under 35 U.S.C. 154(b) by 0 days.

(21) Appl. No.: 09/277,597

(22) Filed: Mar. 26, 1999

Related U.S. Application Data

(63) Continuation-in-part of application No. 08/975,560, filed on Nov. 21, 1997, now abandoned.

(51) Int. Cl.[7] .............................................. B01D 35/143
(52) U.S. Cl. .............................. 96/417; 96/418; 96/419; 55/DIG. 34
(58) Field of Search ........................ 95/25; 55/DIG. 34; 96/417, 418, 419, FOR 170; 116/264, 270; 73/705; 385/12, 13

(56) References Cited

U.S. PATENT DOCUMENTS

| | | | |
|---|---|---|---|
| 4,146,887 A | | 3/1979 | Magnante |
| 4,154,586 A | | 5/1979 | Jones et al. |
| 4,530,706 A | | 7/1985 | Jones |
| 4,699,511 A | | 10/1987 | Seaver |
| 4,735,212 A | | 4/1988 | Cohen |
| 4,834,496 A | | 5/1989 | Blyer, Jr. et al. |
| 4,834,497 A | * | 5/1989 | Angel .......................... 385/12 |
| 4,846,548 A | | 7/1989 | Klainer et al. |
| 5,153,931 A | * | 10/1992 | Buchanan et al. ............. 385/12 |
| 5,250,095 A | | 10/1993 | Sigel, Jr. et al. |
| 5,280,548 A | | 1/1994 | Atwater et al. |
| 5,436,167 A | * | 7/1995 | Robillard ...................... 385/12 |
| H1470 H | | 8/1995 | Ewing et al. |
| 5,512,882 A | | 4/1996 | Stetter et al. |
| 5,796,472 A | | 8/1998 | Wirthlin |
| 5,828,798 A | | 10/1998 | Hopenfeld |

FOREIGN PATENT DOCUMENTS

EP      61884      10/1982

OTHER PUBLICATIONS

K. Ogawa, S. Tsuchiya, H., Kawakami, T. Tsutsui, "Humidity—Sensing Effects of Optical Fibers with Microporous SiO$_2$ Cladding", Electronics Letters, vol. 24, No. 1, pp. 42–43, Jan. 1988.

(List continued on next page.)

Primary Examiner—Robert A. Hopkins
(74) Attorney, Agent, or Firm—Merchant & Gould, P.C.

(57) ABSTRACT

An end-of-service indicator for use with a respirator cartridge, the end-of-service indicator having an optical waveguide having two extremities, one of the extremities being connected to a light source, the other of the extremities being connected to a detector which measures the intensity of light guided and transmitted by the fiber. An alarm is connected to the detector and is triggered when the intensity of light measured by the detector is below a predetermined level. An important aspect of the end-of-service indicator is that at least a portion of the optical fiber is porous. In use, the end-of-service indicator is placed inside a respirator cartridge having a gas/vapor sorbent, so that when the respirator cartridge is used in a toxic environment, the gas/vapor sorbent and the porous glass gradually become saturated. This porous glass will absorb the gas/vapor in the same fashion as the sorbent used in the respirator cartridge, thereby lowering the guiding and transmission properties of the optical fiber which loses the necessary conditions to guide light.

28 Claims, 12 Drawing Sheets

OTHER PUBLICATIONS

C. Richard Hall and Richard J. Holmes, "Degradation in the Performance of Activated Carbon Filters and How to Overcome the Problem", Journal of the International Society for Respiratory Protection, Summer 1992, pp. 6–16.

J.C. Andre, J.P. Sandino, P. Martin, "Detecteur de satiration de filters anti–gaz, Etudes et recherches nouvelles en 1997", Jan. 1997, vol. 4, No. 1, Institut National de Recherches Scientifiques.

S.A. Juchinskii, V.I. Sukhanov, M.V. Khazova and A.V. Dotsenko, "Effective Optical Constants of Porous Glass", Opt. Spectrosc. (USSR) 70 (1), Jan. 1991, pp. 85–88.

K.D. Bennett and A.U. Gencel, "Investigation of Modal Power Distribution in Multimode Fibers used in Multimode Fibers used in Multiple in—line Sensors", Photonics Technology Laboratory, Department of Electrical Engineering, Lafayette College, Easton, PA, 18042–1775, SPIE vol. 2444, pp. 71–82.

* cited by examiner

END-OF-SERVICE INDICATOR INCLUDING POROUS WAVEGUIDE FOR RESPIRATOR CARTRIDGE

RELATED APPLICATION

The present application is a continuation-in-part of Ser. No. 08/975,560 filed Nov. 21, 1997, now abandoned.

FIELD OF THE INVENTION

The present invention is directed to an end-of-service indicator including a porous waveguide, preferably an optical fibre, for the detection of the saturation of a respirator cartridge.

DESCRIPTION OF THE PRIOR ART

Respirator cartridges, and devices which incorporate them, are among the most important security devices used to protect the health of workers. More than 10 million respirator cartridges are used each day in North America.

One of the critical elements related to efficient and safe use of these cartridges is their life span. In the case of gas and vapour pollutants, often the only indicator of the saturation of the cartridge is the odor of the pollutant. This is a dangerous indicator of the end of service of the cartridge since there are many pollutants whose olfactory detection level is below the Threshold Limit Value (TLV). For a user, it is desirable that the cartridge includes an active indicator to indicate without ambiguity that the useful life of the cartridge has ended. In 1984, the National Institute for Occupational Safety and Health (NIOSH) published standards for the certification of active end-of-life indicators to encourage the development of such systems.

One type of active end-of-life indicator presently under investigation is based on the use of polymer films containing carbon particles. The presence of soluble organic vapours causes a change in the resistance of the film and it is this element that is measured. Another type of indicator is described in U.S. Pat. No. 4,146,887 to Magnante, describing the use of a temperature sensor (thermocouple or other) to detect the exothermic reaction of gas/vapour absorption in a respirator cartridge.

A related field to the invention is the field of fiber optic chemical sensor (FOCS). Many articles have been published and several patents awarded for the use of FOCS to detect solvent or chemical products. The vast majority of FOCS use a spectroscopic approach in one form or another, i.e. they rely on light absorption at specific wavelengths to identify chemical species.

Some FOCS measure light loss caused by refractive index change. For instance, U.S. Pat. No. 5,828,798 (HOPENFELD JORAM) describes the use of a specially shaped plastic fiber with a coating that dissolves in the presence of the analyte to be detected. The HOPENFELD patent claims a fiber optic sensor different from other fiber optic sensors in that the cladding material has a refractive index superior to the refractive index of the core, and that the fiber has a specific shape to increase its sensitivity. Furthermore, in the HOPENFELD patent, the cladding is chosen to be specific to a particular analyte and will dissolve in the presence of the analyte. As a result, the light transmitted by the fiber increases in the presence of the analyte.

Few FOCS use porous material, although an article published in Electronic Letters, vol. 24, p. 42 (1988) describes the use of an optical fibre having a porous cladding to measure humidity levels. In this case, the optical fibre is manufactured by depositing porous glass soot on a pure silica fibre. The intensity of the transmitted light decreases by 60% when the relative humidity reaches 90%. In this case, the fibre is straight.

U.S. Pat. No. 5,250,095 (SIGEL JR GEORGE ET AL) describes the use of a porous fiber as a chemical sensor. In this case, the pores are used as an optical chamber to contain the agent which will cause a change in the optical transmission of light by the agent and not because of changes to the guiding properties of the fiber. The SIGEL patent is very similar to standard spectroscopy techniques to detect and identify substances: it uses a tunable narrow-wavelength light source (lamp+monochromator), an optical cell (the porous fiber) and a detector to measure the change in absorption of light as a function of wavelength. The agent(s) of interest for sensing are optically detected.

The following U.S. patents are also of interest:

U.S. Pat. No. 4,154,586 Jones et al. RESPIRATOR CARTRIDGE END-OF-SERVICE LIFT INDICATOR SYSTEM AND METHOD OF MAKING;

U.S. Pat. No. 4,530,706 Jones RESPIRATOR CARTRIDGE END-OF-SERVICE LIFE INDICATOR;

U.S. Pat. No. 4,699,511 Seaver REFRACTION SENSOR;

U.S. Pat. No. 4,834,496 Blyler, Jr. et al. OPTICAL FIBER SENSORS FOR CHEMICAL DETECTION;

U.S. Pat. No. 4,846,548 Klainer FIBER OPTIC WHICH IS AN INHERENT CHEMICAL SENSOR;

U.S. Pat. No. 5,280,548 Atwater et al. EMISSION BASED FIBER OPTIC SENSORS FOR PH AND CARBON DIOXIDE ANALYSIS;

U.S. Pat. No. 5,512,882 Stetter et al. CHEMICAL SENSING APPARATUS AND METHODS;

H1470 Ewing et al. REFRACTIVE INDEX-BASED SENSOR FOR THE DISCRIMINATION OF CHLORINATED HYDRO-CARBONS FROM GROUNDWATER.

SUMMARY OF THE INVENTION

It is an object of the present invention to provide a respirator cartridge having a waveguide end-of-service indicator that is universal, active, unambiguous and simple in its construction. In accordance with the invention, this object is achieved a respirator cartridge having a waveguide end-of-service indicator, the end-of-service indicator comprising a waveguide having two extremities, one of the extremities being connected to a light source, the other of the extremities being connected to a detector which measures the intensity of light transmitted by the waveguide. An alarm is operatively connected to the detector and is triggered when the intensity of light measured by the detector is below a predetermined level. The end-of-service indicator is characterised in that at least a portion of the waveguide is porous. In use, when the end-of-service indicator is placed inside or at the exit of a respirator cartridge having a gas/vapour sorbent, and the respirator cartridge is used in a toxic environment, the gas/vapour sorbent gradually becomes saturated as does the porous waveguide, thereby lowering the guiding and transmission properties of the waveguide and triggering the alarm. In a preferred embodiment, the waveguide is an optical fibre.

BRIEF DESCRIPTION OF THE DRAWINGS

The present invention and its advantages will be more easily understood after reading the following non-restrictive description of preferred embodiments thereof, made with reference to the following drawings, where.

DESCRIPTION OF A PREFERRED EMBODIMENT OF THE INVENTION

The present invention is directed to a respirator cartridge having an end-of-service indicator. The end-of-service indicator generally includes an optical waveguide, although in a preferred embodiment, the waveguide is an optical fibre.

The following description will initially review the basic principles and objects of the invention before describing a preferred embodiment thereof.

The basic principle of optical fibre transmission is based on the guiding of a light beam by total internal reflection. This total internal reflection is possible when the light beam is in a core of index n, surrounded by a cladding of index $n_2$, where $n_1$ is greater than $n_2$ and the angle of incidence of the light beam with respect to normal must be greater than a critical angle which is expressed by the relation as in $(n_2/n_1)$.

Many different configurations are possible to meet these criteria, i.e. the cladding and the core may be manufactured from glass or plastic having different indexes, the core may be glass and the cladding may simply be air and so on. As mentioned previously, the preferred embodiment of the invention includes an optical fibre, although it should be understood that a planar waveguide or other light guiding devices based on the principle of total internal reflection may also be used without departing from the scope of the invention. It should also be understood that, in the present description, when reference is made to light, it is meant to include electromagnetic radiation generally.

Figure 3:
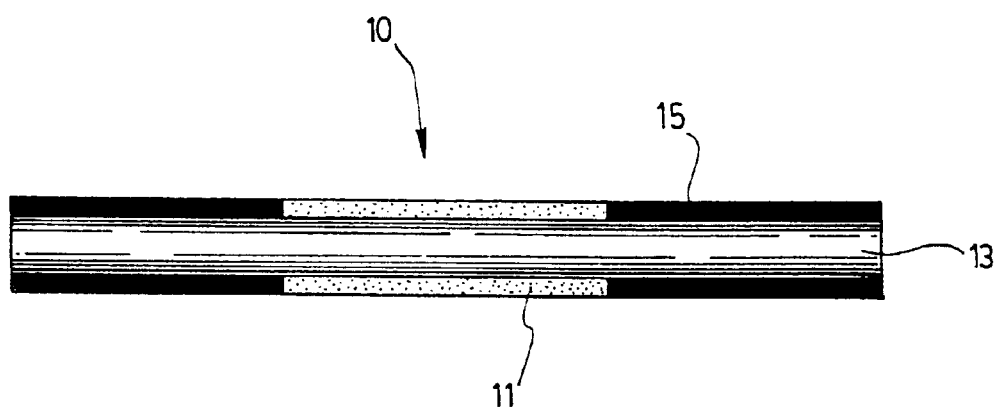
FIG. 3 is a longitudinal cross-section of an optical fibre having a portion of the cladding that is porous.

The optical fibre 10 used for the end-of-service indicator 1 according to the invention is manufactured from porous silica glass. The glass is stretched to obtain fibres of a desired diameter. These fibres are further thermally and chemically treated to transform a part or the whole of the glass into porous glass 11. This porous glass is a plurality of interconnected micro pores having a skeleton of silica glass. The dimension and the density of the pores may thus be partly controlled through thermal treatment. The final result is a fibre that is completely or totally porous or a fibre having a porous cladding 11 and a solid core 13 such as the one illustrated on FIG. 3. If necessary, a slight layer of polymer 15 may be applied on the exterior of the fibre, and a hydrophobic treatment may be applied to the fibre to make it insensitive to water. These processes are well known in the industry, and it should be understood that a critical aspect of the invention is that at least a portion of the optical fibre must be porous as shown on FIG. 3. Any type of porous fibre will meet the objectives of the invention, as long as the proper adjustments are made. Similarly, a planar waveguide, or any other light guiding structure that uses the principle of total internal reflection, with a porous cladding, would also meet the objects of the invention.

Figure 1:
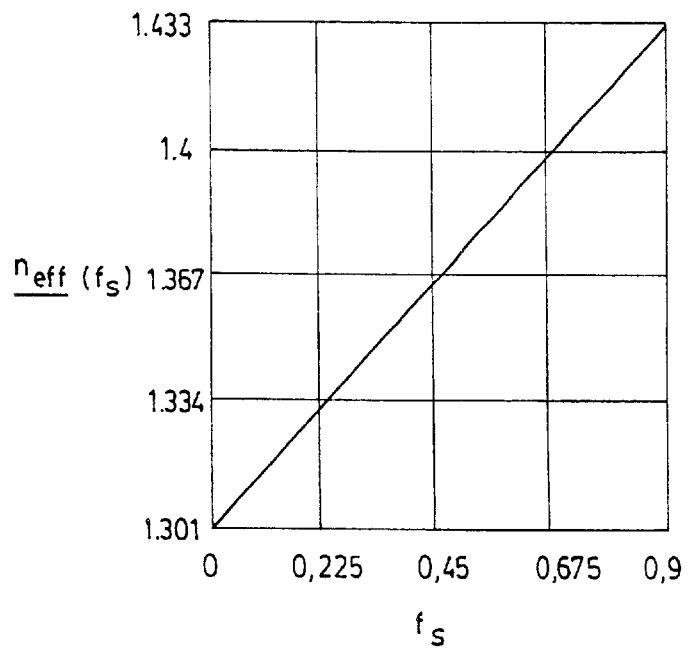
FIG. 1 is a graph showing the effective index of refraction of a porous glass region as a function of the fraction of the porous volume occupied by a solvent.

In the presence of gas and vapours, the pores adsorb this gas and vapour and retain them. The more the pores are filled, the more the index of the porous glass increases. This change in index affects the guiding properties of the fibre and thus these guiding properties become an indication of the adsorption in the pores. FIG. 1 shows the effective index of refraction increase as a function of the volume of pores that is filled with a solvent where $n_{eff}$ is the effective refraction index of the fibre and $f_s$ is the function of porous volume occupied by the solvent.

Figure 2:
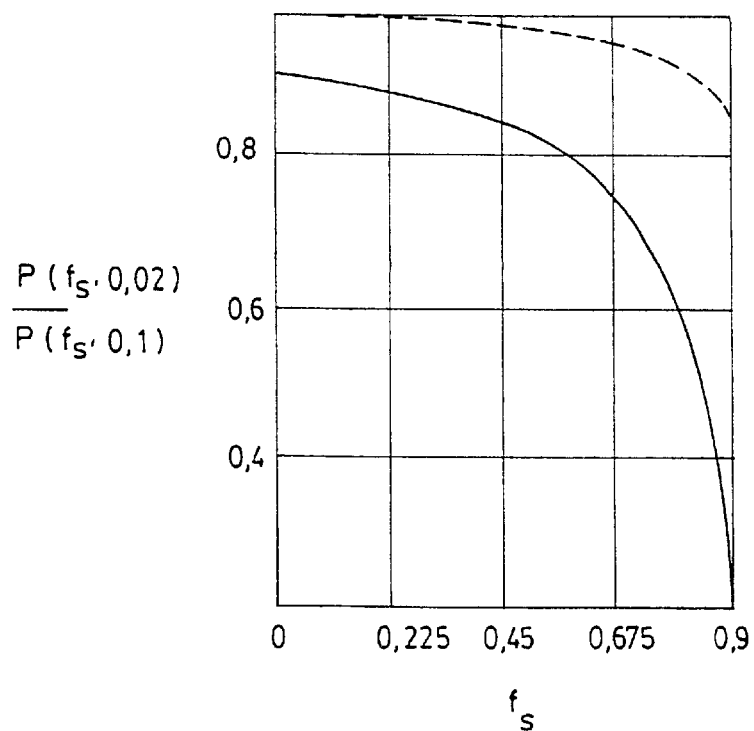
FIG. 2 is a graph showing the fraction of the transmitted power as a function of the porous volume occupied by the solvent, where the transmitted light power also depends on the radius of curvature (R) of the fibre.

The behaviour of the fibre 10 is also a function of the geometrical form of the fibre 10: length and curvature of the fibre 10. The longer the porous section 11 and the greater its curvature, the guiding losses will be increasingly sensitive to the effective index of the porous milieu. In such case, multi-turn fibres 10 of small radius can thus be manufactured and are more sensitive than a straight fibre. FIG. 2 shows how the transmitted power varies as a function of the volume of pores that is filled with a solvent and how this varies as a function of the radius R of curvature of the fibre.

The power transmitted can be expressed as:

$$P(f_s, R) = 1 - \frac{2\frac{a}{R}}{1 - \left(\frac{n_{eff}(f_s)}{n_m}\right)^2}$$

where: $f_s$ is the function of the porous volume occupied by the solvent;

R is the radius of curvature of the fibre;

a is the core radius of the optical fibre;

$n_{eff}$ in the effective index of refraction; and $n_m$ is the refractive index of the silica matrix.

On this FIG. 2, the dotted line represents the power transmitted for a radius of curvature of 10 cm, whereas the solid line represents the power transmitted for a radius of curvature of 2 cm.

Optical fibre indicators as described above can thus be used as end-of-service indicators for respiratory cartridges 100, where the end-of-service indicator comprises an optical fibre 10 having two opposite extremities 21, 23, one 21 of the extremities being connected to a light source 31, the other extremity 23 being connected to a detector 41 which measures the intensity of light transmitted by the fibre. An alarm 51 is operatively connected to the detector 41 and triggered when the intensity of light (or power) measured by the detector 41 is below a predetermined level. The optical fibre 10 is characterised in that at least a portion of the fibre 10 is porous. In use, the end-of-service indicator 1' is placed inside a respirator cartridge 100 having a gas/vapour sorbent 101 so that when the respirator cartridge 100 is used in a toxic environment, the gas/vapour sorbent 101 gradually becomes saturated, thereby lowering the transmission properties of the optical fibre 10. The detector 41 and the light source 31 may be integrated to the fibre or to the electronic module 60. In this last case, optical fibres operatively connect the sensing fibre 10 to the electronic module 60. Various approaches are possible to interface the fibre 10 and the electronic module 60 and which are simple and economical. The fibre 10 itself costs almost nothing when manufactured in great quantities and may be discarded after usage. The electronic module 10 measures the intensity of the light transmitted by the fibre. If such a fibre is exposed to gas vapours 70, the pores of the cladding will fill up through adsorption. It is the same principle as for the activated carbon used in respiratory cartridges. The index of the porous glass will increase as a function of the volume of pores that are saturated by the solvent. This increase of the index will finally affect the guiding properties of the fibre 10 and this effect is increasingly present when the curvature of the fibre is important. An increased curvature of the fibre diminishes the angle of incidence of the light beam and the guiding becomes more and more difficult. In practice, an important decrease of the light transmission is observed when the fibres are exposed to vapours of various solvents. Placing the fibre within the gas/vapour, which is usually activated carbon, ensures that the indicator 1 will react only when the surrounding carbon is saturated. Other configurations are also possible. For example, to avoid throwing the indicator 1 out with each cartridge, the fibre 10 may be sandwiched between a disposable cartridge and a second cartridge which protects the indicator against excess humidity and which protects the user when the disposable cartridge fails.

When the porous fibre adsorbs sufficient gas or vapours, the transmission decreases under a pre-established threshold value and an audible or visual alarm is triggered.

Since the principle of the indicator resides in the phenomenon of adsorption and guiding losses, the indicator is not selective and works with all products susceptible of being absorbed by activated carbon. In fact, the indicator reacts when the porous glass is saturated—which happens when the activated carbon saturates.

Industry standards and practice require that an end-of-service indicated be able to warn the user when the cartridge has reached approximately ninety percent (90%) of its useful life. It must not interfere with the operation of the respiratory cartridge 100. The reference level and its sensitivity must remain stable for long periods of time and it must be responsive to a large array of gas and toxic vapours.

Furthermore, to ensure its commercial success, the production costs must be very low and it must be easily integratable to respiratory cartridges that exist. Further, it is not necessary that the end of service indicator response be linear, although it must be precise and adjustable.

Figure 9A:
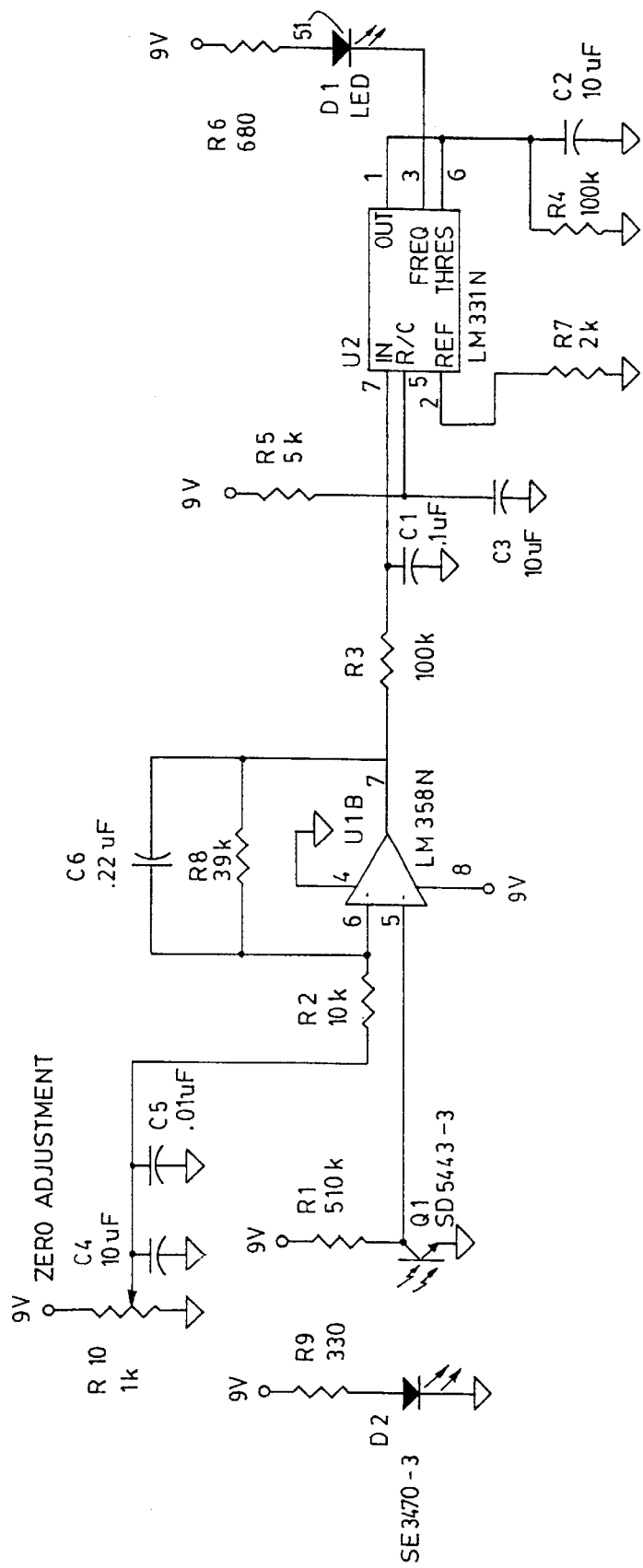
FIG. 9a is a schematic representation of a detector circuit for use with the end-of-life indicator according to the invention.
Figure 9B:
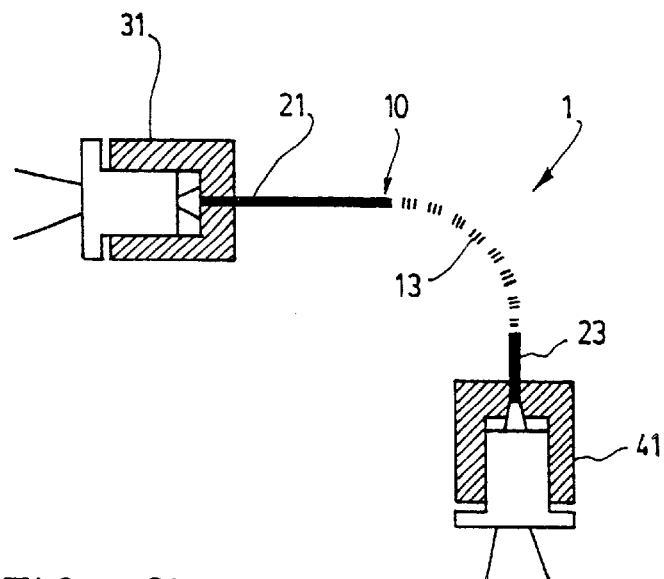
FIG. 9b is a schematic representation of the set-up used for the experimental results.
Figure 10:
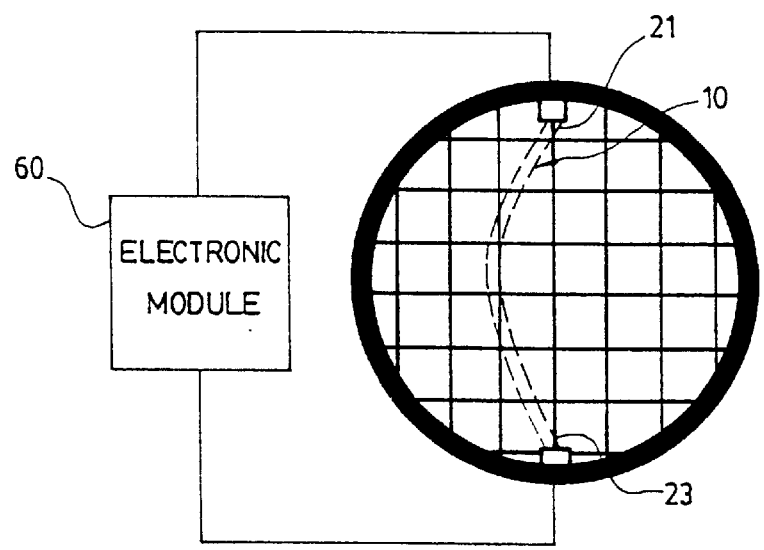
FIG. 10 is a top plan view of the end-of-service indicator according to a preferred embodiment of the invention inserted in a respirator cartridge.
Figure 11:
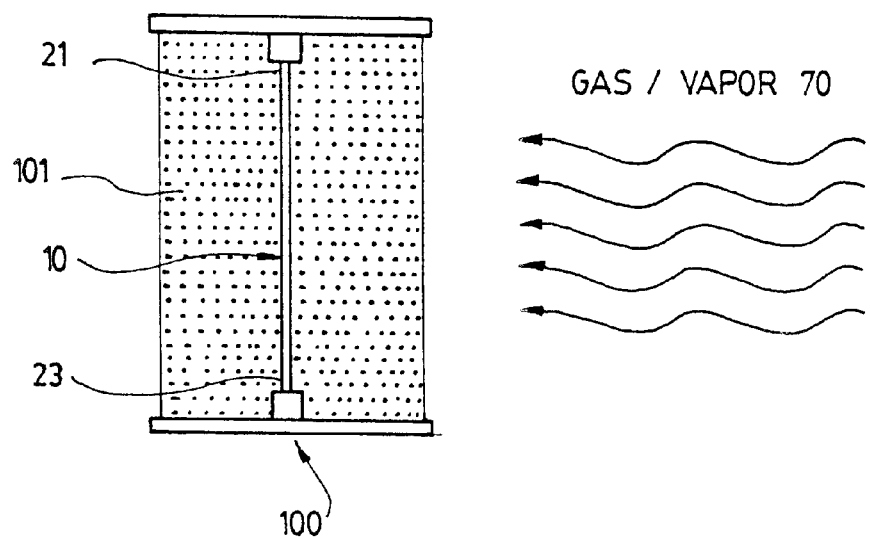
FIG. 11 is a view taken along line XI—XI of FIG. 10.
Figure 12:
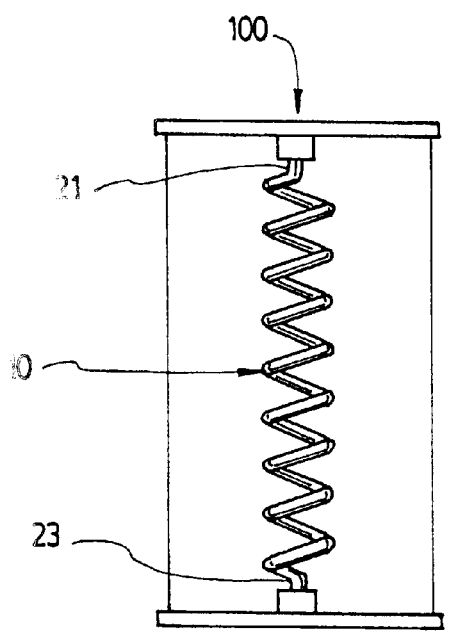
FIG. 12 is an alternative side view of an end-of-service indicator according to another preferred embodiment of the invention.

The experimental equipment used to evaluate performances of the indicator is illustrated on FIG. 9b. The extremities 21, 23 of the fibre are mounted in small aluminium blocks which have the necessary openings to receive the fibre 10 and the detector 41 or the light source 31. It is important to note that the extremities of the fibres are used as is, i.e. without polishing or special preparation. There is no precision adjustment and the fibre is easily installed in the blocks in a few seconds. This fibre remains nonetheless relatively fragile and brittle.

The electronics used for the experiment are shown on FIG. 9a, which is essentially an amplifier followed by a voltage-frequency converter, the latter controlling a LED.

The detector 41 used is a phototransistor (Q1) and the light source is an electrolight diode (D2) in the infrared region (800 nm). These elements were chosen because they represent which is the most common in the area of electro-optical components. They are very cheap as they are used within devices of mass consumption, i.e. infrared remote control. The electronic circuit feeds the light source and measures the power transmitted by the fibre. The electronic card also includes a circuit which triggers a blinking LED (D1). The frequency of the blinking increases when the transmission of the fibre decreases. This allows having visual indication of the state of the fibre. A 9-volt battery supplies the electronics. It should however be understood that any means for evaluating the transmission properties of the fibre would meet the objectives of the invention.

Figure 4:
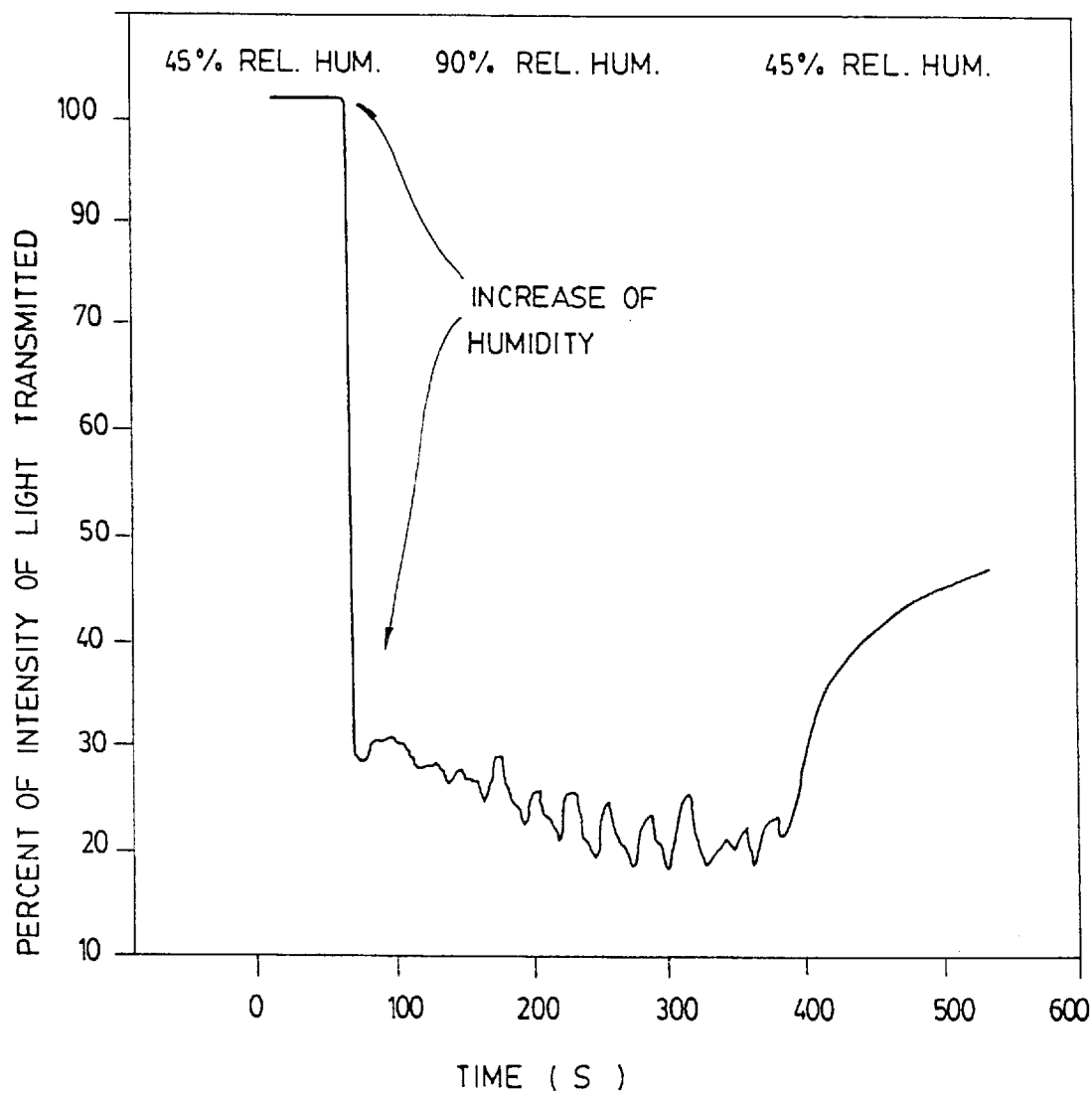
FIG. 4 is a graph showing the percentage of transmitted power when the optical fibre of FIG. 3 is exposed to a humid environment.

FIG. 4 illustrates a first result obtained with the indicator. This graph shows the power transmitted by the fibre 10 when the indicators exposed to a humid environment of 90% relative humidity. For the purposes of this experiment, the indicator was placed in an environmental chamber with automatic control of the relative humidity. The oscillations of the signal at 90% relative humidity are caused by the system of the chamber which continually corrects the degree of humidity by very fine jets of water vapour. When the indicator is replaced into an atmosphere that is less humid, the signal recuperates, but very slowly. In this case, the desorption is a much slower process.

It should be noted that the sensitivity of the porous fibre to water vapour can be detrimental if the respirator cartridge has to be used in a highly humid atmosphere, since there is a risk that the end-of-service indicator will give a false alarm. Accordingly, the porous fibre can be treated with a commercially available hydrophobic coating to inhibit the water adsorption in the pores of the fibre, but without adversely affecting the properties of the porous fibre to detect toxic gas/vapours.

Figure 13:
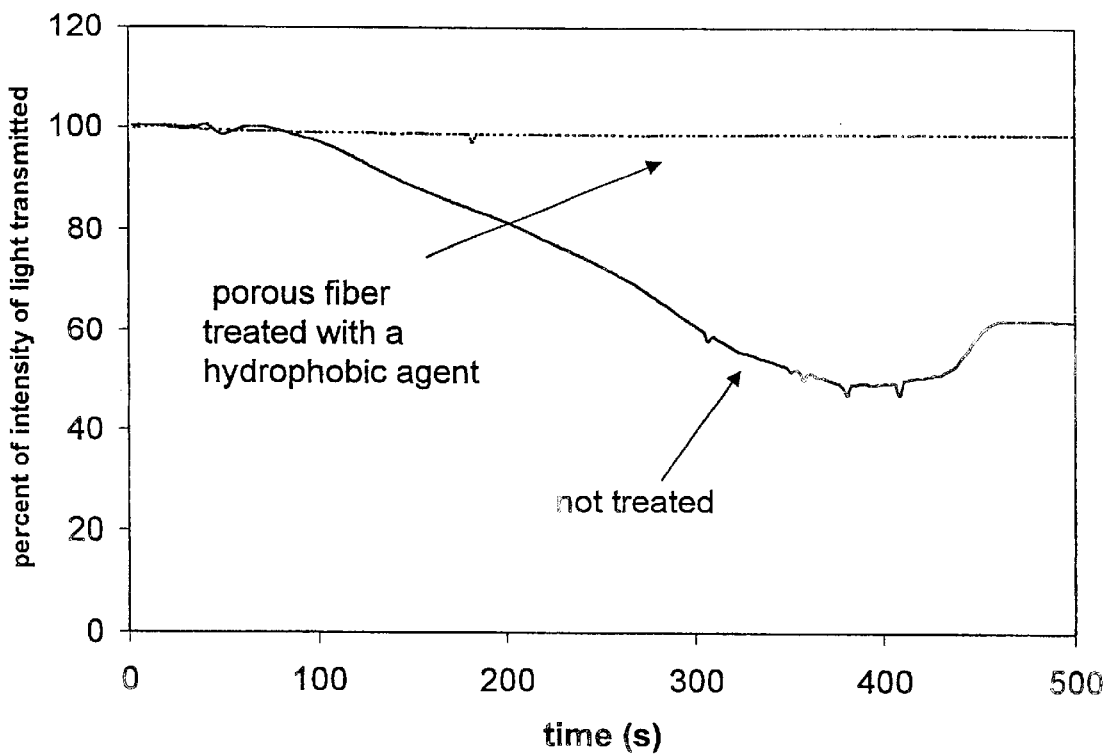
FIG. 13 is a graph showing the percentage of light transmitted for a porous fibre treated with a hydrophobic coating agent and for an untreated porous fibre; both fibers were exposed to a 100% relative humidity level.

FIG. 13 shows experimental results obtained with a porous fibre treated with a hydrophobic agent (dashed line) versus an untreated fibre (solid line). It can be seen that the percentage of light transmitted by the treated fibre is almost unaffected by humidity, whereas the untreated fibre's signal degrades with time. However, it was noted that the presence of a hydrophobic agent creates optical losses within the fibre, but that for an indicator measuring variations in transmitted power, these optical losses were negligible.

Figure 5:
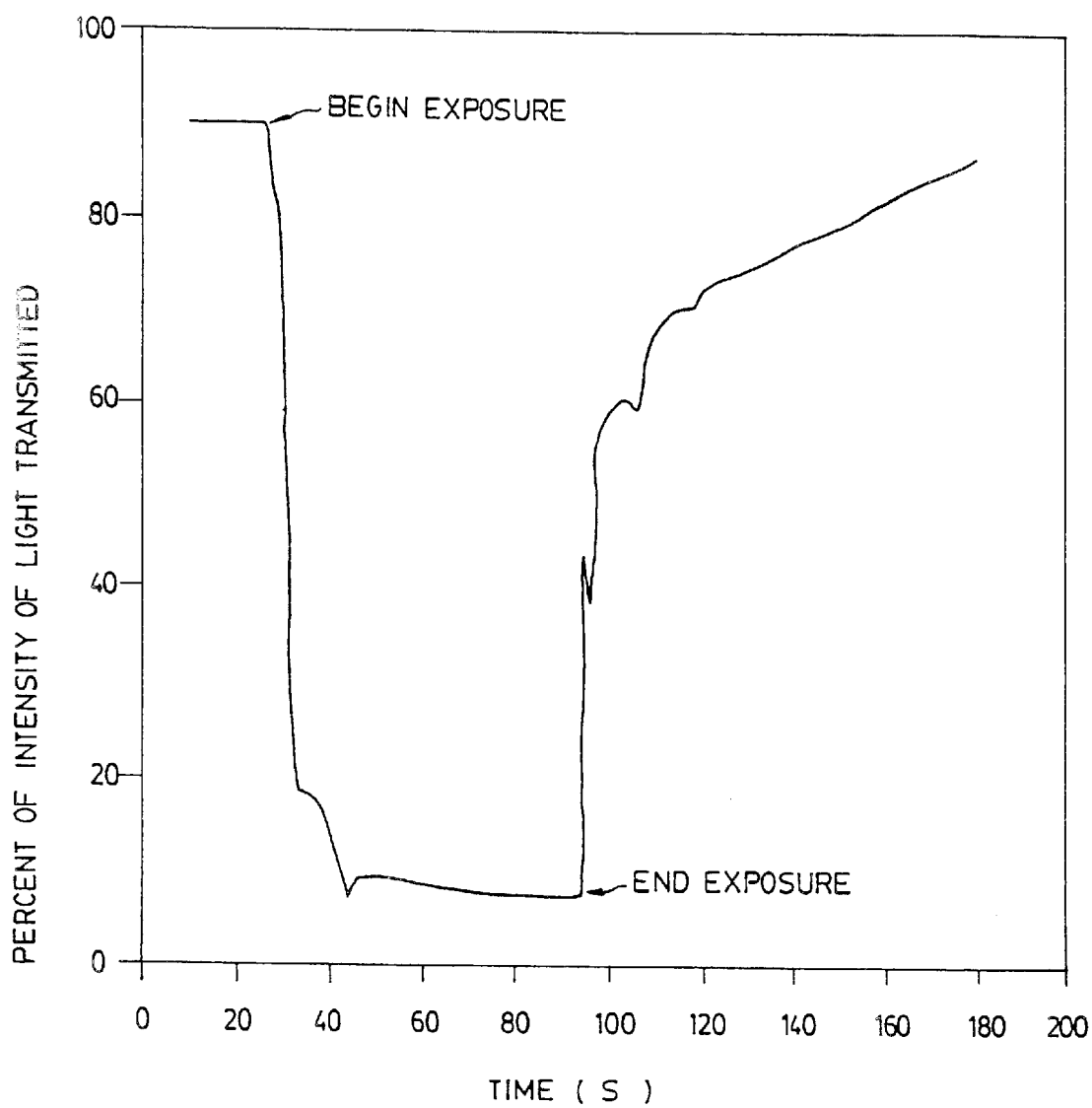
FIG. 5 is a graph showing the percentage of transmitted power when the optical fibre of FIG. 3 is exposed to acetone.

To verify the response of the indicator 1 to vapours of solvents, the indicator 1 was placed in a hermetic box in the presence of an open container containing the solvent. The indicator 1 was thus exposed at concentrations that are relatively high equal to those pressures of vapour of the solvents used. FIG. 5 illustrates the results with a fibre 10 in the presence of acetone. The response of the indicator 1 is very quick as can be seen from this FIG. 5. The recuperating period is also relatively quick but demonstrates a behaviour that is much more complex but is reproducible, at least for the few tries that were made.

Figure 6:
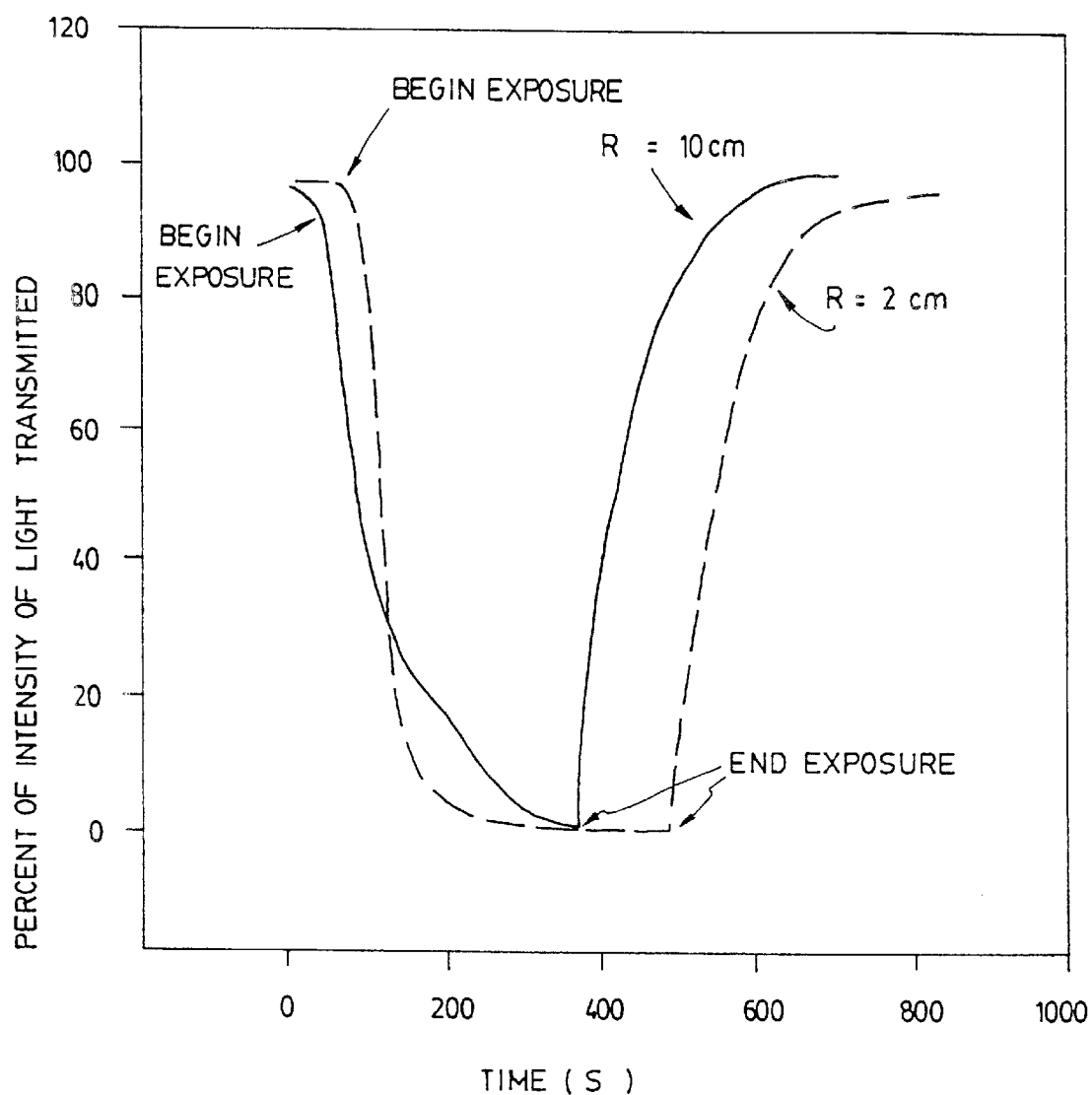
FIG. 6 is a graph showing the percentage of transmitted power when the optical fibre of FIG. 3 is exposed to toluene, and as a function of the radius of curvature of the fibre.

FIG. 6 illustrates the result in the presence of toluene. Here, it is not the choice of the solvent that is significant as the indicator reacts with all of those that were tested (methanol, isopropanol, etc.). This graphic illustrates however the variation of response in function of the curvature of the fibre. With a radius of curvature of 2 cm, the indicator responds more rapidly than with a radius of curvature of 10 cm and is thus more sensitive.

Figure 7:
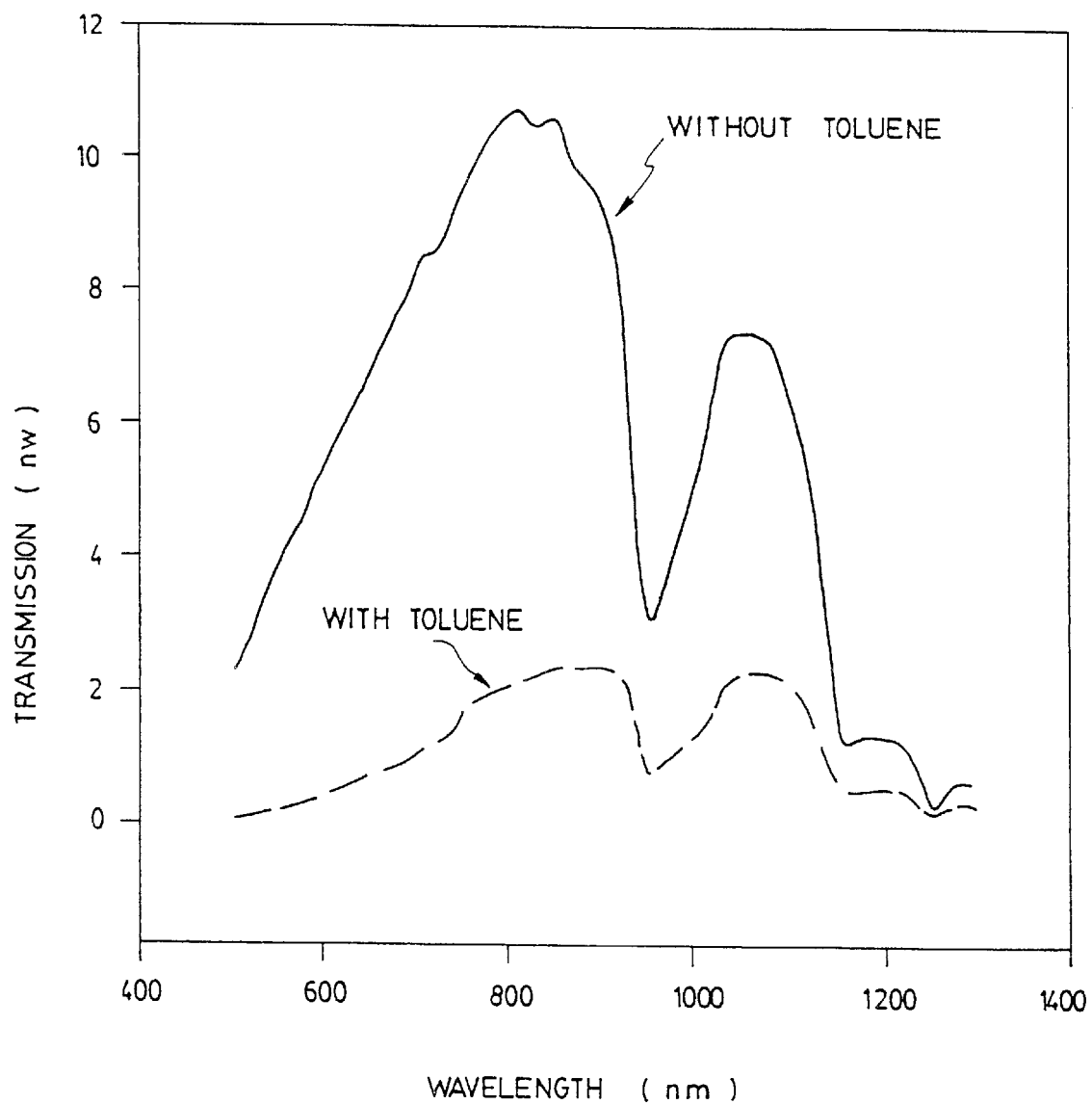
FIG. 7 is a graph showing the transmitted power as a function of the wavelength, without toluene and in the presence of toluene.
Figure 8:
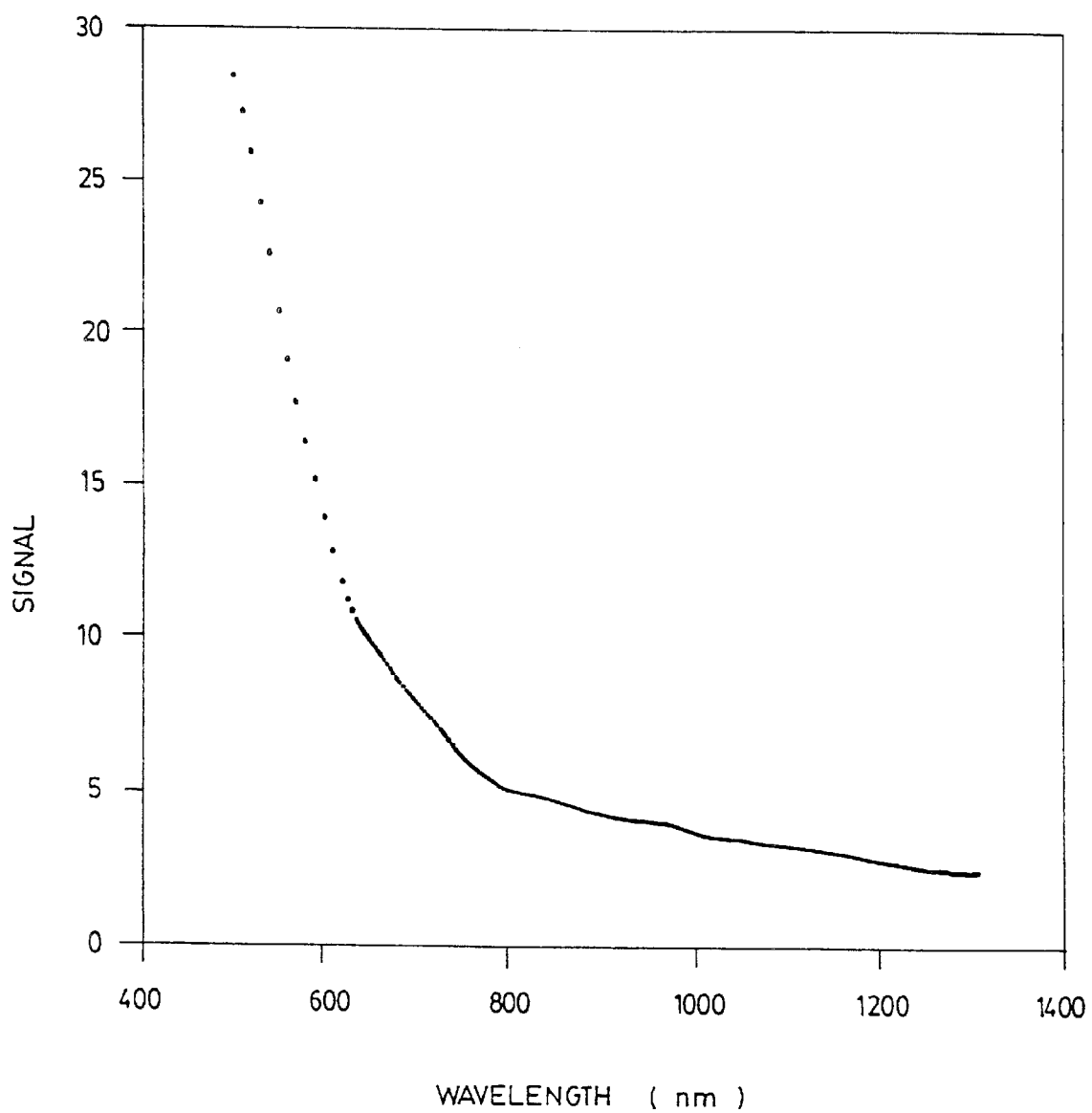
FIG. 8 is a graph showing the ratio of the transmitted power without toluene over the transmitted power with toluene, as a function of the wavelength.

The majority of other approaches which use an optical fibre for chemical detection are very selective and the wavelength that is used is a function of the contaminant that one wishes to detect. On the contrary, the response of the indicator 1 of the present invention is in principle independent of the wavelength used and is non-selective. It is an important advantage that required verification. In order to do so, the light emitting diode (i.e. light source 31) was replaced by a white wide-band source and the output of the fibre was sent to a spectral analyser. The results of these measurements are illustrated on FIG. 7. As expected, there is no specific wavelength at which the indicator does not function. The indicator reacts at all wavelengths. However, the response of the fibre is greater at a shorter wavelength because the guiding properties of the fibre are in function of the wavelength as shown on FIG. 8. The results of FIG. 8 are obtained by plotting the ratio of the transmission without toluene over the transmission with toluene as a function of wavelength.

Figure 14:
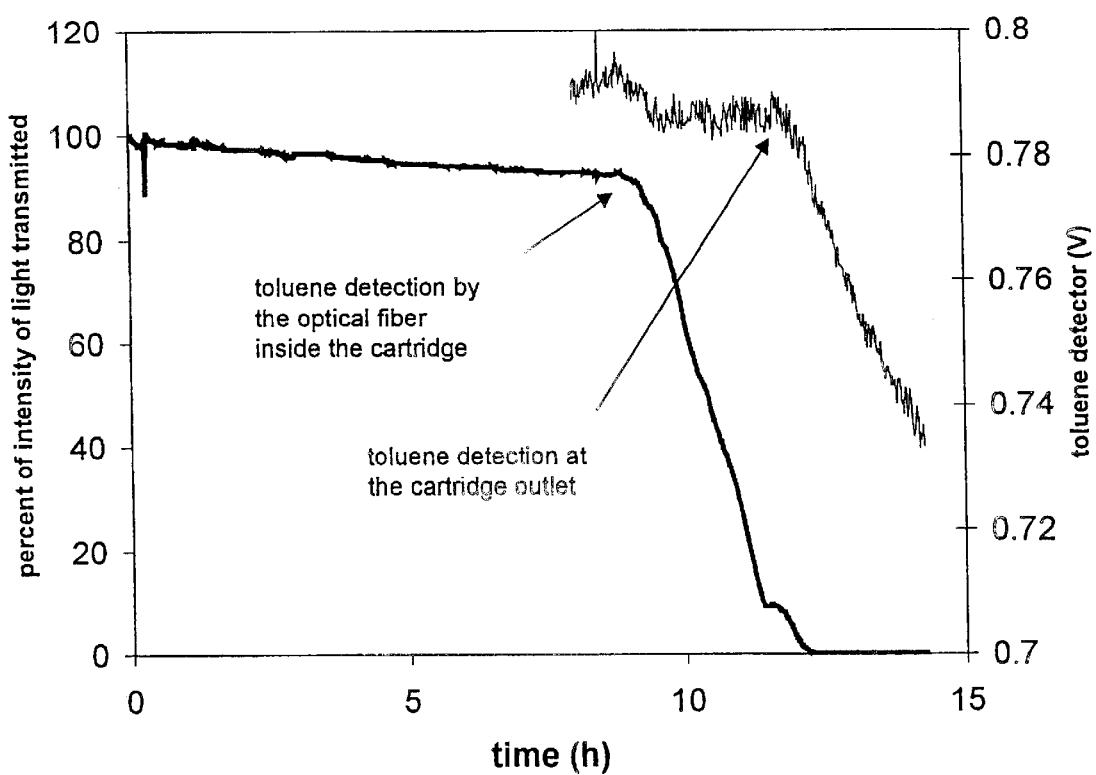
FIG. 14 is a graph showing the percentage of light transmitted for a porous fibre inside a cartridge as a function of time.

Finally, a practical experiment was undertaken, where a porous fibre was placed inside activated carbon. FIG. 14 shows the percentage of light transmitted as a function of time (thick line). In order to evaluate the efficiency of the fibre, a detector was also placed at the outlet or exit of the respirator cartridge, which measured the concentration of toluene at the cartridge outlet. As can be seen, the intensity of light dramatically reduces when the fibre becomes saturated. However, there is a time delay between the fibre saturating and high levels of toluene being present at the outlet of the cartridge. This time delay is due to the fact that the fibre was inserted in the activated carbon. At the location of the fibre, the carbon was saturated but behind the fibre, that is near the outlet, the carbon was not yet saturated and thus still absorbing toluene. This experiment shows that the respirator cartridge according to the invention is a viable device.

An important distinction, after having described the preferred embodiment, can now be made with respect to FOCS addressed in the Description of the Prior Art, above. FOCS and even FOCS which use some form of porous materials are intrinsically different from the end-of-service indicator described herein for the following reasons:

1. These FOCS are designed to detect specific substances, whereas the present invention is designed to be totally non-specific and to respond to all gas/vapours for which the respirator cartridge is to be used;
2. These FOCS use the cladding or the core of the optical fibre as an optical cell, allowing the light to interact directly with the gas, vapours or other chemical species acting as sensitizers. The present invention uses the porous region as a vessel to accumulate relatively large quantities of gas/vapours in the same fashion as the respirator cartridge does; and
3. These FOCS use specific wavelength(s) (or a monochromator or other light dispersive element) to detect specific substances. The present invention will work at any wavelength or combination of wavelengths and requires no filter, monochromator or similar devices.

Furthermore, our end-of-service indicator has a cladding index inferior to the refractive index of the core and no special shape of the fiber is required. Our end-of-service indicator has a non-specific cladding which measure the condensation of gases in the pores of a porous glass. It does not measure the dissolution of the cladding. Moreover, the light transmitted decreases when the analyte is present for our sensor. The end-of-service indicator according to this invention does not detect the agent(s) directly but only detects when the porous glass are filled by this agent. In SIGEL referred to above, claims are made that the invention is reversible, specific and very sensitive. The end-of-service indicator according to this invention is not (and does not need to be) reversible, is not specific and should not be, and does not require to be very sensitive since it does not need to detect minute amount of agent(s) but the cumulative effect of a long exposure to the agent. SIGEL goes on to give example of detection of specific products at a quantitative level (e.g. it can measure the concentration of ammonia in air). In contrast, the present end-of-service indicator does not measure the concentration of any specific product but only indicates when the pores are saturated with the product (any product). The SIGEL patent describes a chemical sensor whereas the present end-of-service indicator is not a chemical sensor but detects the variation of a physical process: the absorption of gas vapor inside a porous structure. Finally, an ageing phenomenon of the fibre has been observed even though quantitative measures on this topic are not available. Without protection from ambient air, the filters that were used lost the majority of their sensitivity after two months. It is believed that this phenomenon is caused by the chemisorption of volatile components normally present in air. However, this ageing phenomenon should not be detrimental to the invention since the porous fiber is protected from contamination by this respirator cartridge itself.

The above experiment shows that the potential of an indicator 1 with an optical fibre 10 having a porous cladding 11 works.

We have demonstrated that it is possible to conceive and manufacture an optical fibre indicator 1 that is very simple and potentially at low-cost. This indicator 1 reacts quickly to the presence of solvents and may be a very good candidate. However, the experiments have dealt mostly with concentrations of solvents that are very high and for very short exposition periods.

We already know that a shorter wavelength, a longer porous section, and a thinner cladding may increase the sensitivity of the indicator. But it is also possible that a different volume of pores, an additional surface treatment or a tighter curvature may also increase the performance of the apparatus.

Although the present invention has been explained hereinabove by way of a preferred embodiment thereof, it should be pointed out that any modifications to this preferred embodiment within the scope of the appended claims is not deemed to alter or change the nature and scope of the present invention.

What is claimed is:

1. An end-of-service indicator for a respirator cartridge having a gas/vapor sorbent, said end-of-service indicator comprising:

a waveguide having two extremities, one of said extremities being connected to a light source, the other of said extremities being connected to a detector, said detector measuring the intensity of light transmitted by said waveguide; and an alarm operatively connected to said detector, said alarm being triggered when the intensity of light measured by said detector is below a predetermined level; wherein at least a portion of said waveguide contains holes;

whereby, in use, when said end-of-service indicator is used in a toxic environment, said portion of said waveguide that contains holes gradually becomes saturated through adsorption, thereby lowering the guiding and transmission properties of said waveguide and triggering the alarm.

2. An end-of-service indicator according to claim 1, wherein said waveguide is an optical fibre.

3. An end-of-service indicator according to claim 2, wherein said fibre has a cladding and a core and said at least one portion of said waveguide that contains holes is said cladding.

4. An end-of-service indicator according to claim 2, wherein said fibre has a cladding and a core and said at least one portion of said waveguide that contains holes has said cladding and said core.

5. An end-of-service indicator according to claim 3, wherein said optical fibre further includes a polymer coating.

6. An end-of-service indicator according to claim 2, wherein said at least one portion of said waveguide that contains holes has a predetermined length.

7. An end-of-service indicator according to claim 2, wherein said optical fibre is straight.

8. An end-of-service indicator according to claim 2, wherein at least one portion of said fibre is cork-screwed.

9. An end-of-service indicator according to claim 2, wherein:

said light source is a LED;

said detector includes a light sensor, having an output which is operatively connected to an amplifier, said amplifier being operatively connected to a voltage-frequency converter; and said alarm is a visual alarm consisting of a LED.

10. An end-of-service indicator according to claim 3, wherein said optical fibre is straight.

11. An end-of-service indicator according to claim 4, wherein said optical fibre is straight.

12. An end-of-service indicator according to claim 5, wherein said optical fibre is straight.

13. An end-of-service indicator according to claim 6, wherein said optical fibre is straight.

14. An end-of-service indicator according to claim 3, wherein a portion of said fibre is cork-screwed.

15. An end-of-service indicator according to claim 4, wherein a portion of said fibre is cork-screwed.

16. An end-of-service indicator according to claim 5, wherein a portion of said fibre is cork-screwed.

17. An end-of-service indicator according to claim 6, wherein a portion of said fibre is cork-screwed.

18. An end-of-service indicator according to claim 3, wherein:

said light source is a LED;

said detector includes a light sensor having an output which is operatively connected to an amplifier, said amplifier being operatively connected to a voltage-frequency converter; and said alarm is a visual alarm consisting of a LED.

19. An end-of-service indicator according to claim 4, wherein:

said light source is a LED;

said detector includes a light sensor having an output which is operatively connected to an amplifier, said amplifier being operatively connected to a voltage-frequency converter; and said alarm is a visual alarm consisting of a LED.

20. An end-of-service indicator according to claim 5, wherein:

said light source is a LED;

said detector includes a light sensor having an output which is operatively connected to an amplifier, said amplifier being operatively connected to a voltage-frequency converter; and said alarm is a visual alarm consisting of a LED.

21. An end-of-service indicator according to claim 6, wherein:

said light source is a LED;

said detector includes a light sensor having an output which is operatively connected to an amplifier, said amplifier being operatively connected to a voltage-frequency converter; and said alarm is a visual alarm consisting of a LED.

22. An end-of-service indicator according to claim 9, wherein said optical fibre is treated with a hydrophobic coating.

23. An end-of-service indicator according to claim 18, wherein said optical fibre is treated with a hydrophobic coating.

24. An end-of-service indicator according to claim 19, wherein said optical fibre is treated with a hydrophobic coating.

25. An end-of-service indicator according to claim 20, wherein said optical fibre is treated with a hydrophobic coating.

26. An end-of-service indicator according to claim 21, wherein said optical fibre is treated with a hydrophobic coating.

27. An end-of-service indicator according to claim 1, wherein said holes include a plurality of interconnected micro-pores having a skeleton.

28. An end-of-service indicator according to claim 27, wherein said skeleton is a skeleton of silica glass.

* * * * *

UNITED STATES PATENT AND TRADEMARK OFFICE
CERTIFICATE OF CORRECTION

PATENT NO. : 6,375,725 B1
DATED : April 23, 2002
INVENTOR(S) : Bernard et al.

It is certified that error appears in the above-identified patent and that said Letters Patent is hereby corrected as shown below:

<u>Title page,</u>
Item [54], Title, insert -- A -- after the word "INCLUDING"
Item [73], Assignees, "Santa" should read -- Santé --

Signed and Sealed this

Twenty-second Day of October, 2002

*Attest:*

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO. : 6,375,725 B1
DATED : April 23, 2002
INVENTOR(S) : Bernard et al.

It is certified that error appears in the above-identified patent and that said Letters Patent is hereby corrected as shown below:

<u>Title page,</u>
Item [54], Title: insert -- A -- after the word "INCLUDING"
Item [73], Assignees: "Santa" should read -- Santé --

Signed and Sealed this

Twenty-ninth Day of October, 2002

Attest:

Attesting Officer

JAMES E. ROGAN
*Director of the United States Patent and Trademark Office*